(12) United States Patent
Aeschlimann et al.

(10) Patent No.: US 11,998,297 B2
(45) Date of Patent: Jun. 4, 2024

(54) TREATMENT PARAMETERS FOR ACOUSTIC WAVE STIMULATION

(71) Applicant: Creaholic S.A., Biel (CH)

(72) Inventors: Marcel Aeschlimann, Ligerz (CH); Carole Chapelat, Biel (CH); Naomi Bitmead, Bremgarten bei Bern (CH); Samuel Malzach, Evilard (CH); Martin Sigrist, Bern (CH); Yann Schaeffer, Lichtensteig (CH); Laurent Torriani, Lamboing (CH); Rafael Luca Zuber, Bolligen (CH); Loïc Sottas, Lausanne (CH)

(73) Assignee: CREAHOLIC S.A., Biel (CH)

( * ) Notice: Subject to any disclaimer, the term of this patent is extended or adjusted under 35 U.S.C. 154(b) by 350 days.

(21) Appl. No.: 17/441,855

(22) PCT Filed: Mar. 25, 2020

(86) PCT No.: PCT/EP2020/058440
§ 371 (c)(1),
(2) Date: Sep. 22, 2021

(87) PCT Pub. No.: WO2020/193667
PCT Pub. Date: Oct. 1, 2020

(65) Prior Publication Data
US 2022/0183560 A1  Jun. 16, 2022

(30) Foreign Application Priority Data
Mar. 25, 2019 (CH) .................................. 00394/19

(51) Int. Cl.
*A61B 5/00* (2006.01)
*A61B 5/055* (2006.01)
(Continued)

(52) U.S. Cl.
CPC .......... *A61B 5/0036* (2018.08); *A61B 5/0064* (2013.01); *A61B 5/055* (2013.01);
(Continued)

(58) Field of Classification Search
CPC ..... A61B 5/0036; A61B 5/0064; A61B 5/369; G16H 20/40
See application file for complete search history.

(56) References Cited

U.S. PATENT DOCUMENTS

2005/0277824 A1 12/2005 Aubry et al.
2014/0228721 A1* 8/2014 Ehrenreich ........ A61H 23/0245
601/47
(Continued)

FOREIGN PATENT DOCUMENTS

JP   2017-536925 A   12/2017
WO   02/058791       8/2002
(Continued)

OTHER PUBLICATIONS

Japanese Office Action dated Dec. 5, 2023, Application No. 2021-557196; English translation included, 14 pages.

*Primary Examiner* — Gerald Johnson
(74) *Attorney, Agent, or Firm* — Rankin, Hill & Clark LLP

(57) ABSTRACT

A method for cell stimulation by mechanical energy as well as a method for determining a subject specific set of treatment parameters for acoustic wave stimulation and a method for validating a set of treatment parameters for acoustic wave stimulation. The method for determining a subject specific set of treatment parameters includes generating subject specific data, which includes measuring a geometric property of a body portion, and determining a target field distribution in the body portion. The method for validating a set of treatment parameters for acoustic wave stimulation includes determining a target field distribution of an acoustic
(Continued)

Figure 1:
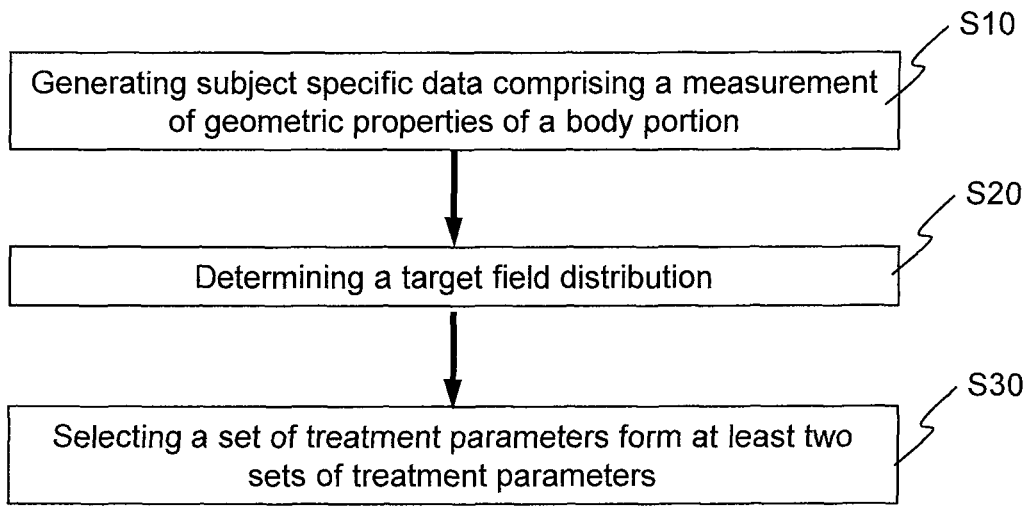

field in a body portion, receiving a related set of treatment parameters for at least one transducer, generating a subject specific 3D model of the body portion, and determining a difference between the target field distribution and a field distribution determined in the subject specific 3D model.

14 Claims, 6 Drawing Sheets

(51) Int. Cl.
  *A61B 5/107* (2006.01)
  *A61B 5/369* (2021.01)
  *A61B 8/08* (2006.01)
  *A61N 7/00* (2006.01)
  *G16H 20/40* (2018.01)

(52) U.S. Cl.
  CPC ............ *A61B 5/1079* (2013.01); *A61B 5/369* (2021.01); *A61B 5/6802* (2013.01); *A61B 8/0808* (2013.01); *A61N 7/00* (2013.01); *G16H 20/40* (2018.01); *A61N 2007/0013* (2013.01); *A61N 2007/0026* (2013.01); *A61N 2007/0095* (2013.01)

(56) References Cited

U.S. PATENT DOCUMENTS

| | | | |
|---|---|---|---|
| 2017/0291044 A1 | 10/2017 | Zheng et al. | |
| 2020/0129237 A1* | 4/2020 | Ay | A61B 5/01 |
| 2022/0062660 A1* | 3/2022 | Verner Rashkovsky | A61N 7/00 |

FOREIGN PATENT DOCUMENTS

| | | |
|---|---|---|
| WO | 2004/019784 | 3/2004 |
| WO | 2010/036732 | 4/2010 |
| WO | 2013/192582 | 12/2013 |

* cited by examiner

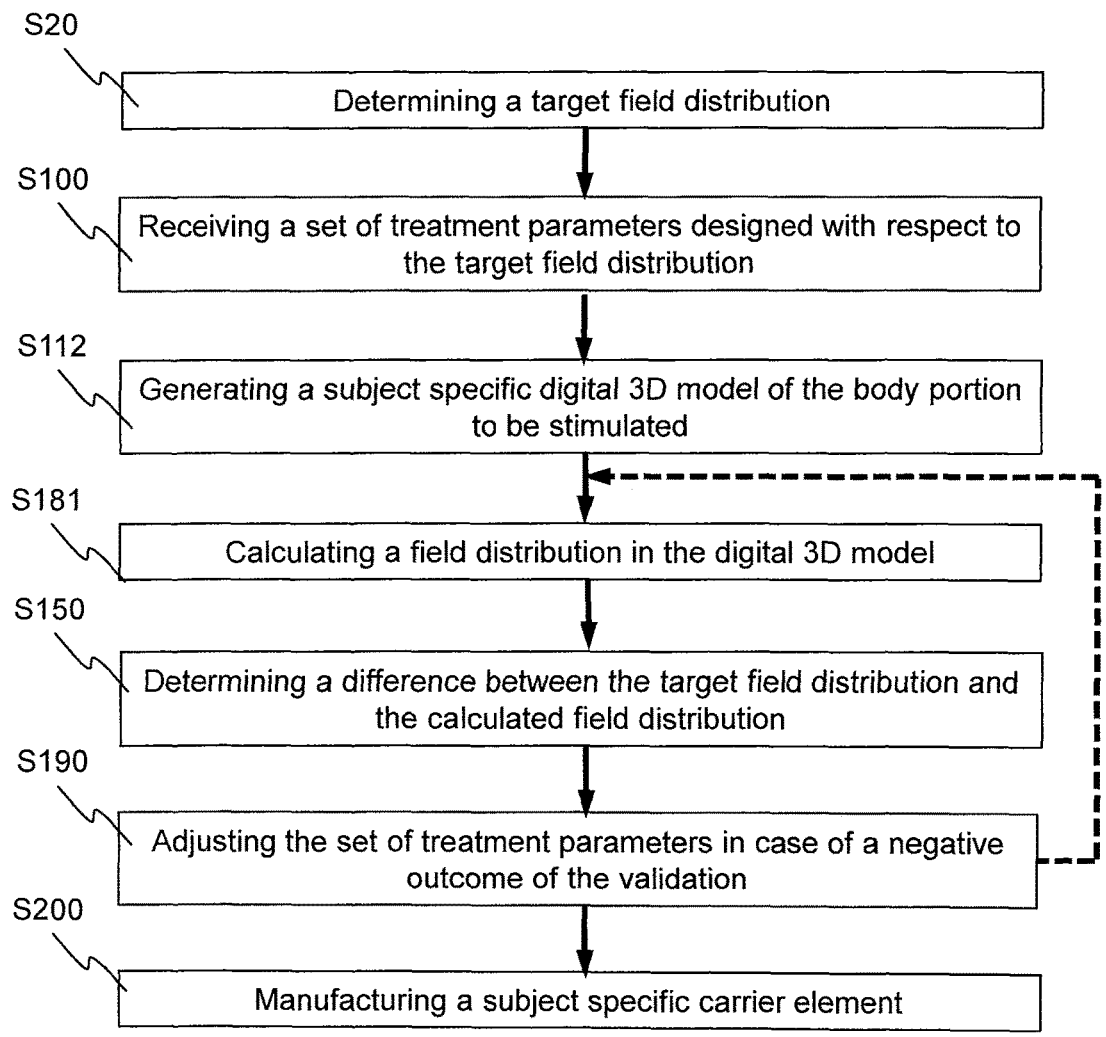
Fig. 8
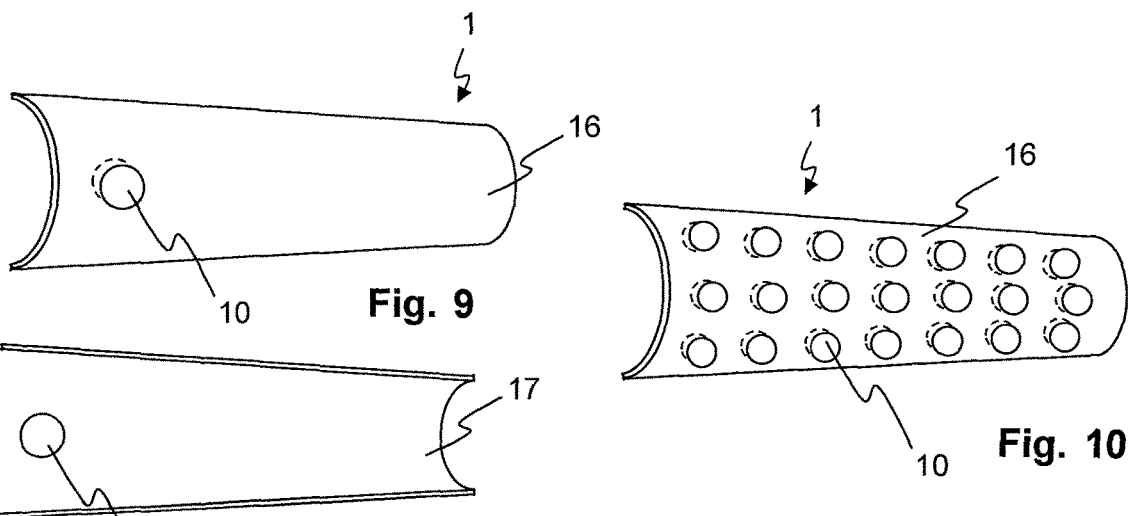
Fig. 9
Fig. 10

TREATMENT PARAMETERS FOR ACOUSTIC WAVE STIMULATION

BACKGROUND OF THE INVENTION

Field of the Invention

The invention relates to the field of cell stimulation by mechanical energy, in particular by acoustic energy, for example stimulation by ultrasound, such as focused ultrasound (FUS). It relates to a method for determining treatment parameters, to a method for validating and—if needed—adjust treatment parameters and to devices related to such methods.

Related Art

US 2017/0291044 A1 discloses an ultrasound deep brain stimulation method and an ultrasound deep brain system. The method disclosed is a time reversal method and includes the steps of creating a head 3D digital model from image data of the head of the animal or human being that needs ultrasound deep brain stimulation, creating a 3D digital model of an ultrasound transducer array, and determining a voltage signal to be applied to the "real" ultrasound transducer array used to generate a specific ultrasound field in the brain by placing virtual sound sources at one or more positions that need to be focused, simulating propagation behaviour of ultrasound wave emitted from the virtual sound sources in the head 3D digital model, and simulating a voltage signal of the ultrasound transducer array when the ultrasound wave is propagated to a virtual spatial position where the ultrasound transducer array is located. In an embodiment, a model of the skull is printed, "real" sound sources are placed at one or more positions that need to be focused, and the voltage generated by an ultrasound transducer array arranged on the printed skull is measured in order to determine the voltage signal to be applied to the ultrasound transducer array.

Independent of the embodiment of the ultrasound deep brain stimulation method disclosed in US 2017/0291044 A1, the head of the animal or human being is placed in a magnetic resonance imaging (MRI) system during ultrasound transmission in order to observe and adjust position displacement and shape change of the focus point.

State of the art methods for cell stimulation by acoustic waves as disclosed in US 2017/0291044 A1 have various drawbacks. In particular, the determination of treatment parameters includes complex simulations and/or complex measurements that can be configured and carried out by experts, only. Further, there is need in such state of the art methods to place the head of the animal or human being in an MRI system, which prevents the method from being used outside a specialized medical facility and from being used for medical cases that are often rated as less severe, such as medical cases related to muscular tension, migraine, tension/relaxation, learning problems, sleep problems, etc. Even further, the components of the system used to carry out state of the art methods for cell stimulation by acoustic waves have a very specific design that can be adapted to medical cases in a limited manner only and have a user-friendliness that is very limited.

In other words, state of the art methods and devices are too complex, too expensive and too limited in design and realization to be used by a wider public and/or for a wide range of applications, this means for a wide range of medical and non-medical cases.

Applications in the fields of brain therapy, trauma treatment (e.g., bone stimulation, muscle stimulation), pain treatment (e.g., chronic pain, back pain, migraine) or drug delivery (e.g., localized drug delivery, gene therapy) are examples of applications related rather to medical cases. Applications in the fields of wellbeing (e.g., relaxation, less severe cases of insomnia, migraine and muscular tension, etc) or learning are examples of applications related rather to non-medical cases.

SUMMARY OF THE INVENTION

It is an object of the invention to overcome drawbacks of state of the art methods and devices.

In particular, it is a first object of the invention to provide a method for determining a subject specific set of treatment parameters for acoustic wave stimulation and related devices that can be used by the wider public for a wide range of applications.

It is a second object of the invention to provide a method for validation and—if needed adjustment—of a set of treatment parameters for acoustic wave stimulation and related devices that can be used by the wider public for a wide range of applications.

Independent of the aspect of the invention and of embodiments thereof, the following terms have the following meaning if not stated explicitly otherwise:

An object, such as a set of treatment parameters or a body portion, is "subject specific" if it is related to an individual (human or animal) subject, such as a patient. For example, measures can have been taken to make sure that the object is related or adapted to an individual patient.

A "set of treatment parameters for acoustic wave stimulation" (in short "treatment parameters") include operating parameters of the transducer(s) used to generate an acoustic field in the body portion to be stimulated and information concerning the arrangement of the transducer(s) relative to the body portion (to a physical 3D model thereof, as the case may be). The latter can include information concerning at least one of an orientation of the transducer(s) with respect to the body portion, a contact pressure between the transducer(s) and the body portion, and the type of transducer to be used, for example. The orientation of a transducer can be given by the angle between an axis, in particular an oscillation axis, of the transducer and the surface normal of the body portion at the position at which the transducer is arranged, for example. Frequency, intensity, pulse duration, pulse length, pulse repetition rate are examples of operating parameters.

The treatment parameters can also include information concerning the arrangement of transducers relative to each other if more than one transducer is used.

A "body portion" can be any body portion, for example the head, the neck, an extremity or a part thereof.

A "wearable device" is a device that can be arranged on and fixed to the body portion, for example by tightening around the body portion. A hood, a cuff or any other article of clothing that can be arranged around a body portion are examples of a wearable device.

The wearable device can include a rigid portion. The rigid portion can include a surface that forms the negative of a surface of the body portion to be stimulated. The body portion to be stimulated and hence said surface are subject specific in many embodiments.

According to a first aspect of the invention a method for determining a subject specific set of treatment parameters for acoustic wave stimulation as described in the following is provided. Such a method can be realised in combination with a method for validation and—if needed adjustment—of a set of treatment parameters for acoustic wave stimulation according to a second aspect. This means that the treatment parameters determined by the method according to the first aspect of the invention can be validated and adjusted (if needed) by the method according to the second aspect of the invention.

A method according to the first aspect is capable to determine a subject specific set of treatment parameters for acoustic wave stimulation, this means acoustic wave treatment. The method includes the steps of:

Generating subject specific data, wherein the step of generating subject specific data includes measuring at least one geometric property of a body portion.
  The body portion of which the geometric property is measured is the body portion to which the acoustic wave will be applied.
  In embodiments, a plurality of geometric properties is measured.

Determining a target field distribution of an acoustic field in the body portion, wherein the step of determining a target field distribution includes selection of an application, this means of the medical or non-medical case to be treated.
  The target field distribution can be a target intensity distribution.

Selecting a set of treatment parameters from at least two different sets of treatment parameters, wherein the step of selecting is made prior to a step of applying any set of treatment parameters to the body portion.

In the step of selecting a set of treatment parameters from at least two different sets of treatment parameters, a criterion for selecting a set of treatment parameters can be an expected field distribution in the body portion when applied to the body portion.

In particular, the set of treatment parameters can be selected that is expected to approximate best the target field distribution when applied to the body portion.

In an embodiment, the step of selecting includes a comparison of a first expected field distribution related to a first set of treatment parameters with the target field distribution and a comparison of a second expected field distribution related to a second set of treatment parameters.

Each comparison can result in a value indicating the difference between the expected field distribution and the target field distribution, wherein it is the set of treatment parameters related to the expected field distribution having the smaller value that is selected.

In an embodiment, the step of determining the target field distribution can include the substep of consulting an electronic library ("library" in the following).

The library can include entries that relate applications, in particular an effect that should result from the acoustic wave stimulation, to target field distributions.

The entries can further relate subject specific data to target field distributions. The subject specific data can include information as given above.

The entries can further relate target field distributions to sets of treatment parameters.

Each set of treatment parameter can be linked to at least one of a measured or calculated field distribution. A basic number of data sets can be provided by the operator of the library. Further data sets can be provided by users uploading their measurements and calculations (for example the results of the numerical simulation described below).

The library can further include entries concerning:
  Number of successful and unsuccessful use of a set of treatment parameters.
  Measurements of neural activities and/or electrical activities.

The library, or rather a computerized device that hosts the library and/or that is in communication to the library, for example a computer, can be configured to carry out the step of determining the target field distribution.

In an embodiment, the method includes the step of transmitting the subject specific data to the library, wherein the library (the computerized device) is configured to carry out the step of determining the target field distribution.

The selected application can be transmitted to the library, too. Alternatively, the library (the computerized device) can be configured to provide a user interface. The user interface can be configured to allow for a selection of a possible application by a user.

A list of selectable application can depend on the user. The list of selectable applications presented to an expert, such as a practitioner, can include applications, in particular medical applications, that are not selectable in the list presented to a non-expert user.

The step of determining the target field distribution can include the substep of determining the target field distribution that fits best to the subject specific data transmitted to the library. In particular, the determined target field distribution fits best with respect to the target field distributions stored in the library.

In an embodiment, the step of determining the target field distribution does not include the substep of consulting a library. In this embodiment, a practitioner or a user, e.g., supported by material accompanying a device for acoustic wave stimulation or provided in another manner (e.g., on a webpage), can determine the target field distribution.

In embodiments including the substep of consulting a library, the library, or rather the computerized device that hosts the library and/or is in communication to it, can be further configured to carry out the step of selecting a set of treatment parameters.

In this embodiment, the step of selecting can include a substeps of identifying the stored sets of treatment parameters having measured and/or calculated field distributions that fit best the target field distribution and selecting the set of treatment parameters that is predicted to produce the field distribution most suitable for the application.

The prediction can consider at least one of:
  A difference in the geometric property of the measured body portion to be stimulated and the body portion related to the target field distribution determined.
  A difference in at least one of the other subject specific data transmitted.
  A difference in tissue characteristics measured on the body portion to be stimulated and tissue characteristics measured on or estimated for the body portion related to the target field distribution determined.
  An observed deformation of the geometric property of the body portion caused by a wearable device and/or at least one transducer used for stimulation, as described below.
  The measured position of the at least one transducer used for stimulation, as described below.

In particular, the field distribution is predicted to be most suitable for the application compared to other field distributions stored.

The step of generating subject specific data can include a step of collecting subject specific information such as gender, age, weight, height, BMI, body fat content, fat percentage, muscle percentage, etc.

In an embodiment, at least one of the geometric property measured in the step of generating subject specific data and subject specific information as exemplarily given above is considered in the step of selecting a set of treatment parameters.

In other words, characteristics of the body and/or body portion to be treated are considered for selecting a set of treatment parameters.

Optionally, the application selected is considered in addition in the step of selecting a set of treatment parameters.

Hence, the step of selecting a set of treatment parameters can be based on historical treatment data, wherein the set of treatment parameters is selected that was used successfully for that treatment stored that is closest to the selected application and the subject to be treated.

The historical treatment data can be stored in the library.

At least some of the subject specific information can be generated by a wearable device that is equipped accordingly.

In embodiments, the measurement of the geometric property of the body portion includes a measurement of the shape of the body portion. The shape can be measured by a method including at least one of the following steps, for example:

Taking at least two pictures of the body portion, wherein the two pictures are taken from different positions relative to the body portion.

Providing a wearable device including positioning points and/or an arrangement of lines and determining the relative position of the positioning points and/or the course of the lines after arranging the wearable device on the body portion.

Said wearable device can be the same wearable device that is equipped to generate subject specific information different from the geometric property.

Applying acoustic waves to the body portion and measuring the transmitted and/or scattered acoustic waves.

The acoustic waves can be generated and measured by transducers arranged in a wearable device. This wearable device can be the wearable device including the positioning points and/or an arrangement of lines, the wearable device being equipped to generate subject specific information different from the geometric property, the wearable device including the positioning points and/or an arrangement of lines and being equipped to generate subject specific information different from the geometric property, or another wearable device.

Using at least one of an MRI system, CT system and a body scanner.

This embodiment of the step of measuring geometric property can be carried out during a consultation in a medical facility, whereas other steps of the method and the acoustic wave stimulation of a body portion and for an application determined by the subject (e.g., patient) can be carried out without presence of medical experts, for example at home.

The step of measuring geometric property of the body portion can further include the measurement or at least the estimation of the shape of a portion of the body portion, for example the measurement of the shape of a bone, such as the skull or a long bone.

The step of measuring a geometric property of a body portion can generate data representing the 3D geometrical properties, in particular the 3D shape of the body portion and optionally the portion of the body portion measured.

In the step of determining a target field distribution of an acoustic field in the body portion, the target field distribution can be one of the target field distribution in a body corresponding to the geometric property measured, the target field distribution in a body approximating the geometric property measured, and a target field distribution in a stored body that is similar to a body corresponding to the geometric property measured.

Independent of the embodiment, the target field distribution can include information about the acoustic field over an extended area of the body. In particular, the target field distribution can include information about the acoustic field at a plurality of positions in the body, for example more than 10, more than 50 or more than 100 positions.

Independent of the concrete embodiment, the method can include a step of measuring neuronal activity of the body portion and/or measuring electrical activity of the body portion.

This step can be carried out by a method includes at least one of:

Carrying out Electroencephalography (EEG).

Performing functional magnetic resonance imaging (fMRI).

Measuring the Doppler effect.

Carrying out Electrocorticography (ECoG).

The step of measuring neuronal and/or electrical activity of the body portion can be performed during the consultation in a medical facility, whereas other steps of the method and the acoustic wave stimulation of a body portion and for an application determined by the subject can be performed without presence of medical experts, for example at home.

The step of measuring neuronal and/or electrical activity of the body portion can be used to generate a subject specific target field distribution by considering the neuronal conditions of the subject.

The step of measuring neuronal and/or electrical activity of the body portion can be used in a feedback loop used to verify that a field distribution applied to the body portion ("applied field distribution") has the field distribution needed for the desired application, this means for the desired effect.

The step of measuring neuronal and/or electrical activity of the body portion can be used in a feedback loop used to adjust a field distribution applied to the body portion ("applied field distribution"). For example, it can be used to bring the applied field distribution in better agreement with the target field distribution and/or to maximize the effect desired by the stimulation.

The library, the computerized device that hosts the library and/or is in communication to the library, the wearable device or a separate device capable to connect to at least one of the library, the computerized device and the wearable device can include a user interface designed for guiding the subject to the target field distribution that fits best to the desired application.

The wearable device can be any of the wearable devices described above or the wearable device used to generate the acoustic waves for stimulation.

However, a wearable device can be equipped to carry out all steps needed for acoustic wave stimulation of the body portion, including all steps needed for any embodiment of the method for determining a subject specific set of treatment parameters.

In an embodiment, the method includes a step of adding tissue characteristics of the body portion to the measured geometric property.

In particular, acoustic properties of the body portion are added.

In an embodiment, the method includes the step of measuring the tissue characteristics of the body portion. Said step of measuring can be performed prior to the step of adding.

The tissue characteristics can be measured by a method including at least one of the following steps, for example:

Applying acoustic waves to the body portion and measuring the transmitted and/or scattered acoustic waves.

For example, the scattering properties, attenuation and/or speed of sound can be determined. In particular, said properties can be determined in a position dependent manner.

A wearable device including transducers and being equipped to generate and measure acoustic waves can be provided. The transducers and optionally other means to generate and measure acoustic waves can be comprised by any wearable device described above. However, the wearable device including transducers and being equipped to generate and measure acoustic waves can be a separate device.

Applying light tomography.

The steps of measuring and adding tissue characteristic can be performed during the consultation in a medical facility, whereas other steps of the method and the acoustic wave stimulation of a body portion and for an application determined by the subject can be performed without presence of medical experts, for example at home.

In an embodiment, the method includes the step of receiving tissue characteristics from a library, for example the electronic library described above.

Therefore, the step of adding tissue characteristic can include the substep of connecting to the library and downloading information related to tissue characteristics.

The step of receiving tissue characteristics from the library can include the substep of transmitting subject specific data to the library.

Embodiment including the step of adding tissue characteristics can further include a step of generating a digital 3D model of the body portion based on the measured geometric property and on the added tissue characteristics.

The digital 3D model of the body portion can include or be data representing a multi-material (multi-tissue) model of the body portion.

The step of generating a digital 3D model can be performed during the consultation in a medical facility, whereas other steps of the method and the acoustic wave stimulation of a body portion and for an application determined by the subject can be performed without presence of medical experts, for example at home.

In particular, embodiments including the step of generating a digital 3D model can further include the steps of:

Determining a first set of treatment parameters.

Calculating a calculated field distribution of the acoustic field in the body portion using the digital 3D model of the body portion and the first set of treatment parameters.

For example, a numerical simulation using the digital 3D model of the body portion and the first set of treatment parameters is carried out to calculate the calculated field distribution of the acoustic field in the body portion.

A calculated intensity distribution is calculated in embodiments in which the target field distribution is a target intensity distribution.

Examples of numerical simulation methods than can be used in the step of running a numerical simulation are Finite Element (FE), Finite Differences (FD), Finite Integrals (FI), Boundary Element (BE).

Determining a difference between the calculated field distribution and the target field distribution.

The difference can be a set of values, wherein each value represents the difference at a point in the digital 3D model. For example, if the calculated field distribution is calculated by a numerical simulation, the points can be nodes used in the numerical simulation or a selection thereof and corresponding points in the target field distribution.

The set of values can be generated by averaging the calculated field distribution and the target field distribution over the same area.

Adjusting the first set of treatment parameters to a second set of treatment parameters. The adjustment of the first set of treatment parameters can depend from the fulfilment of a condition. For example, the first set of treatment parameters is adjusted to the second set of treatment parameters if the set of values is larger than a preset set of values or if a value derived from the set of values is larger than a preset value.

In particular, the first set of treatment parameters is adjusted to the second set of treatment parameters based on the difference between the calculated field distribution and the target field distribution determined.

In an embodiment, the determined difference between the calculated field distribution and the target field distribution is transmitted to the library and the step of adjusting the first set of treatment parameters to a second set of treatment parameters includes the substep of receiving the second set of treatment parameters from the library.

The step of adjusting the first set of treatment parameters can include an adjustment of the first set of treatment parameters by a practitioner, an experienced user or the subject.

The step of adjusting the first set of treatment parameters can include an adjustment of the first set of treatment parameters in an automated manner.

Optionally, a calculated field distribution of the acoustic field in the body portion using the digital 3D model of the body portion and the adjusted set of treatment parameters can be calculated.

A difference can be determined between the calculated field distribution of the adjusted set of treatment parameters and the target field distribution.

The difference between the calculated field distribution of the adjusted set of treatment parameters and the target field distribution can be used for a further adjusting step.

The steps of calculating a calculated field distribution of an adjusted set of treatment parameters, of determining a difference between the calculated field distribution and the target field distribution, and of adjusting the set of treatment parameters can be repeated several times.

In embodiments including the step of determining a first set of treatment parameters and the step of adjusting the first set of treatment parameters to a second set of treatment parameters, it is often the second set of treatment parameters that is selected in the step of selecting a set of treatment parameters. However, the step of selecting a set of treatment parameters is a step of selecting a set of treatment parameters from the first set of treatment parameters and the second set of treatment parameters in these embodiments.

In the step of determining a first set of treatment parameters, the first set of treatment parameters can be received from a library.

Alternatively, the first set of treatment parameters can be a preset set of treatment parameters that can depend on at least one of the body portion and a position of the at least one transducer used for stimulation on the body portion. In this embodiment, there is no need for a library to be involved in the step of determining the first set of treatment parameters, at least.

In embodiments in which the target field distribution is determined by the use of a library, the first set of treatment parameters can be related to said target field distribution and hence to the application and the subject specific data optionally transmitted to the library.

In an embodiment, the method can include the step of providing a wearable device including at least one transducer and the step of arranging the wearable device at the body portion.

In such an embodiment, the step of determining a first set of treatment parameters can include the substep of reading out a position of the at least one transducer relative to the body portion.

For example, the at least one transducer is equipped to generate the acoustic wave for stimulation and the first set of treatment parameters is determined after the step of arranging the wearable device at the body portion and after the substep of reading out, this means determining, the position of the at least one transducer on the body portion.

In embodiments including the step of arranging the wearable device at the body portion and the substep of reading out the position of the at least one transducer equipped for stimulation, the method can include the further step of determining a deformation of the geometric property of the body portion caused by the wearable device and/or the at least one transducer.

A comparison between the data representing the 3D geometrical properties generated in the step of measuring a geometric property and the position of the at least one transducer can be used for the determination of the deformation.

Alternatively, the comparison can be between the digital 3D model and the position of the transducer.

Optionally, the method can include a routine adapting the digital 3D model if a deformation of the geometric property of the body portion is observed. At least one of the following can be adapted: the geometric property given in the digital 3D model and the tissue characteristics used in the 3D model.

In embodiments in which no tissue characteristic is added to the measured geometric property, the data representing the geometrical properties can be adapted if a deformation of the geometric property of the body portion is observed.

The position of the at least one transducer can be transmitted to the library. It can be a selection criteria to identify the operating parameters of the at least one transducer that is expected to generate a field distribution that is closest to the target field distribution. In particular, the operating parameters are closest to the target field distribution with respect to other operating parameters stored in the library for the same or a similar position of the at least one transducer.

In an embodiment, the first set of treatment parameters received from the library includes both operating parameters and a target position of the at least one transducer.

In this embodiment, the wearable device can be equipped for positioning the at least one transducer in the target position.

Independent of the embodiment, said wearable device can further include at least one of the positioning points and/or the arrangement of lines, the transducers used to generate and measure the acoustic waves in the step of measuring a geometric property, the transducers used to generate and measure the acoustic waves in the step of measuring tissue characteristics, and the means for determining the subject specific data.

In the step of calculating a calculated field distribution of the acoustic field in the body portion using the digital 3D model of the body portion and the first set of treatment parameters, the first set of treatment parameters can be used to determine the excitation of the body portion represented by the digital 3D model.

The step of calculating a calculated field distribution, for example the numerical simulation comprised therein, can be repeated for different sets of treatment parameters. Thereby, a plurality of calculated field distribution, each of it linked to a specific set of treatment parameters, can be produced. The step of selecting a set of treatment parameters from at least two different sets of treatment parameters can then include the selection of one of these specific sets of treatment parameters.

For example, the specific set of treatment parameters is selected that has a calculated field distribution having a difference to the target field distribution that is smaller than a preset value. The preset value can be a set of preset values. The set of preset values can be a preset distribution of maximal differences, for example.

The preset value (the set of preset values) can be set in relation to the difference (the set of values) described above with respect to the step of determining a difference between the calculated field distribution and the target field distribution.

The preset value (the set of preset values) can define a local or global stop condition for the repetition of the calculation for different sets of treatment parameters.

The calculations can be iteratively, wherein the repetition of the calculation is stopped as soon as a global and local variation of the calculated field distribution of two subsequent iteration steps is smaller than preset global and/or local values.

In an embodiment, the step of calculating a calculated field distribution, the step of determining a difference between the calculated field distribution and the target field distribution and the step of adjusting are repeated until the difference between the calculated field distribution and the target field distribution is smaller than a preset value.

In other words, the preset value defines a stop condition for the repetition of said steps.

The preset value defining the stop condition can be received from the library.

For example, the calculation is repeated in an iterative manner.

The calculation can include a numerical simulation or consist of a numerical simulation.

In embodiments in which the target field distribution is received from a library, the preset value can be related to the target field distribution and hence to the application and possibly to the subject specific data if transmitted to the library.

The preset value can be a set of values adapted to the set of values defining the difference between the calculated field distribution and the target field distribution.

The preset value can represent a global stop condition and/or local stop conditions. The latter can be defined by the set of values.

Further embodiments are evident from the dependent patent claims.

According to a second aspect of the invention, a method for validation of a set of treatment parameters for acoustic wave stimulation as described in the following is provided. Such a method can be realised in combination with the method according to the first aspect. However, the method according to the second aspect of the invention can be used to validate treatment parameters that are not generated by a method according to the first aspect, as pointed out in detail below.

The method according to the second aspect can be extended by an adjustment step. In this case, the second aspect concerns a method for validation and adjustment of a set of treatment parameters for acoustic wave stimulation.

A method according to the second aspect is capable to validate—and optionally adjust—a subject specific set of treatment parameters for acoustic wave stimulation. The method includes the steps of:

Determining a target field distribution of an acoustic field in a body portion to be stimulated.
The step of determining a target field distribution can be carried out in any embodiment of the corresponding step of the first aspect.

Receiving a set of treatment parameters for at least one transducer, wherein the set of treatment parameters is designed with respect to the target field distribution.
In particular, the set of treatment parameters is designed to approximate the target field distribution as good as possible with the information at hand and the procedure chosen to design the set of treatment parameters.
For example, the set of treatment parameters is selected from various possible sets of parameters to approximate the target field distribution as good as possible.
For example, the set of treatment parameters is selected that is expected to approximate the target field distribution best. The selection can depend on experience. The experience can be stored and/or provided to a practitioner or patient, for example.

Generating a subject specific 3D model of the body portion to be stimulated.

Determining a difference between the target field distribution and a field distribution determined in the subject specific 3D model.
The field distribution determined in the subject specific 3D model can be a field distribution calculated, for example simulated, in the subject specific digital 3D model or a field distribution measured in the subject specific physical 3D model, for example.

In embodiments including the step of receiving a set of treatment parameters for at least one transducer, the set of treatment parameters is received from an electronic library ("library" in the following), in particular from a library as described with respect to the first aspect.

In such embodiments, the set of treatment parameters received can be the set of treatment parameters stored in the library that are related to a field distribution that fits best the target field distribution.

In embodiments, the set of treatment parameters are calculated, for example by using a numerical simulation.

In particular, the set of treatment parameters can be determined by using numerical simulations.

For some applications, it can be possible to solve the so-called inverse problem. This means that for some applications it can be possible to calculate, for example by numerical simulations, a set of treatment parameters from the target field distribution.

For applications for which the inverse problem cannot be solved, the calculation, the numerical simulation as the case may be, can base on a subject specific or a non subject specific digital model of the body portion. A first set of treatment parameters can be received from the library, can be determined by a practitioner or can be determined by the patent. The first set of treatment parameters can be used to determine a first excitation of the model of the body portion. In such embodiments, the calculation, the numerical simulation as the case may be, gives a first calculated field distribution in the subject specific or non subject specific digital model of the body portion.

A second set of treatment parameters can be determined based on the first calculated field distribution, in particular based on a comparison between the first calculated field distribution and the target field distribution.

The second set of treatment parameters can result from an adjustment of the first set of treatment parameters, wherein the adjustment reduces a difference between a field distribution (in the body portion) related to the second set of treatment parameters and the target field distribution.

A second calculation, a second numerical simulation as the case may be, can be carried out to confirm that the second set of treatment parameters leads to a second calculated field distribution that is closer to the target field distribution than the first calculated field distribution.

A third set of treatment parameters can be determined from the second calculated field distribution in order to reduce a difference between a field distribution (in the body portion) related to the third set of treatment parameters and the target field distribution.

At least one further calculation (numerical simulation as the case may be) can be carried out to confirm that the third—or a further as the case may be—set of treatment parameters leads to a third (further) calculated field distribution that is closer to the target field distribution than the second (previous) calculated field distribution.

In other words, the steps of adjusting a set of treatment parameters, determining a calculated field distribution related to the adjusted set of treatment parameters can be carried out in a repetitive, for example iterative, manner.

Supplementary material providing information relating applications with sets of treatment parameters and target field distributions can be provided to support the practitioner and/or the subject (e.g., patient) in determining a target field distribution and/or a set of treatment parameters.

A set of treatment parameters determined in this manner can be the set of treatment parameters received in the step of receiving a set of treatment parameters.

The at least one transducer is equipped to generate acoustic waves suitable to stimulate the body portion to be stimulated.

The at least one transducer can be arranged or arrangable in a wearable device.

In an embodiment including the step of generating a subject specific 3D model of the body portion to be stimulated, the subject specific 3D model can be a subject specific physical 3D model.

The subject specific 3D model can be the subject specific physical 3D model independent of the embodiment of the step of receiving a set of treatment parameters. In particular, the subject specific 3D model can be the subject specific physical 3D model independent of the manner the set of treatment parameters is determined.

The physical 3D model is a real, this means non-virtual, model of the body portion to be stimulated.

The subject specific physical 3D model has geometric properties that correspond to geometric properties measured on the body portion of the subject to be stimulated. Ideally, it is composed of materials that mimic the physical properties, in particular the acoustic properties, of the tissue of the subject.

The geometric property or properties and the tissue characteristics can be measured in any manner described with respect to the first aspect.

The method can include a step of measuring a geometric property of the body portion, for example in any embodiment as described with respect to the first aspect.

The method can include a step of measuring tissue characteristics of the body portion, for example in any embodiment as described with respect to the first aspect.

In an embodiment including the step of generating a subject specific 3D model of the body portion to be stimulated, the subject specific 3D model can be a subject specific digital 3D model, in particular a digital 3D model as described with respect to the first aspect.

In an embodiment, the subject specific 3D model is the subject specific physical 3D model and the method includes the further steps of:

Providing a wearable device including the at least one transducer.
  The wearable device can be equipped to stimulate the body portion.
  The wearable device can be the wearable device equipped (used) to generate the acoustic waves for stimulation in any embodiment describe with respect to the first aspect.
Arranging the wearable device on the physical 3D model.
  The wearable device can include fixation means.
  The wearable device can include means to arrange it on the physical 3D model and/or on the body portion to be stimulated in a reproducible manner.
Applying the set of treatment parameters to the wearable device.
  The set of treatment parameters include operating parameters of the at least one transducer and information concerning the arrangement of the at least one transducer to the body portion (to the physical 3D model, as the case may be).
  The wearable device and the at least one transducer can be equipped for the at least one transducer being arranged relative to the body portion (to the physical 3D model) according to the set of treatment parameters.
  Alternatively, the at least one transducer can be arranged on the wearable device in a fixed manner and the related position relative to the body portion (the physical 3D model) can be a fixed parameter that has been considered as fixed parameters in the previous steps, too.
  However, the fixed parameter can depend on the application, the body portion and subject specific data (including one or more measured geometric properties of the body portion).
Determining the field distribution generated by the arranged wearable device and the set of parameters applied to the arranged wearable device by a measurement.
  The measurement can include reading out a grid of sensors integrated in the physical 3D model or moving a sensor to different positions in the physical 3D model, for example.

In embodiments, the set of treatment parameters received is a set of treatment parameters determined according to any embodiment of the method for determining a subject specific set of treatment parameters for acoustic wave stimulation, (i.e. of the method according to the first aspect).

The method for validating a set of treatment parameters for acoustic wave stimulation can include any step related to the method according to the first aspect. In particular, the method for validating a set of treatment parameters for acoustic wave stimulation can include any combination of steps related to an embodiment of the method according to the first aspect.

As mentioned, the method according to the second aspect can be extended by an adjustment step. This means that the method can include a step of adjusting the received set of treatment parameters, in an embodiment.

The step of adjusting can include a substep of determining a difference between the target field distribution and the field distribution determined in the subject specific 3D model.

The step of adjusting can be omitted if the difference is smaller than a preset value.

The step of adjusting can be repeated, for example carried out in an iterative manner. Therein, the set of treatment parameters adjusted in the preceding repetition (iteration) can be applied in the repetition (iteration) subsequent to the preceding repetition (iteration).

The repetition (iteration) can stop if the difference between the target field distribution and the field distribution determined in the subject specific 3D model for a set of treatment parameters is smaller than a preset value.

The set of treatment parameters determined or validated by the methods described can be used by a treatment device, such as the wearable device.

The treatment device can be configured to carry out the methods described in any embodiment.

The treatment device includes a carrier element to which the at least one transducer is mounted or to which the at least one transducer is mountable, for example by the carrier element including at least one fixation element.

The carrier element can be equipped to be fastened on the body portion to be stimulated.

Treatment devices and carrier elements are described in detail in the application entitled "Treatment devices for acoustic wave stimulation" filed by the same applicant at the same date as the present application. The disclosure of said application is hereby incorporated by reference.

However, the digital 3D model generated can be used to produce a subject specific carrier element if the digital 3D model includes a model of the surface of the body portion to be stimulated or a portion thereof.

The carrier element produced by the use of the digital 3D model includes a rigid portion having a surface that forms the negative of a surface of the body portion to be stimulated. In other words, the rigid portion includes a surface that is formed according to the surface of the body portion or a portion of the surface of the body portion. This means that the surface of the carrier element fits to the surface of the body portion.

The carrier element can be produced by a rapid manufacturing process, such as milling, turning, casting or an additive manufacturing process such as printing, for example 3D-printing.

Generally, the carrier element and the treatment device are not only wearable but also portable by the subject.

In particular, the carrier element (treatment device) is portable due to its size and weight.

The carrier element, in particular the rigid portion, can be made of light-weight material.

Figure 2:
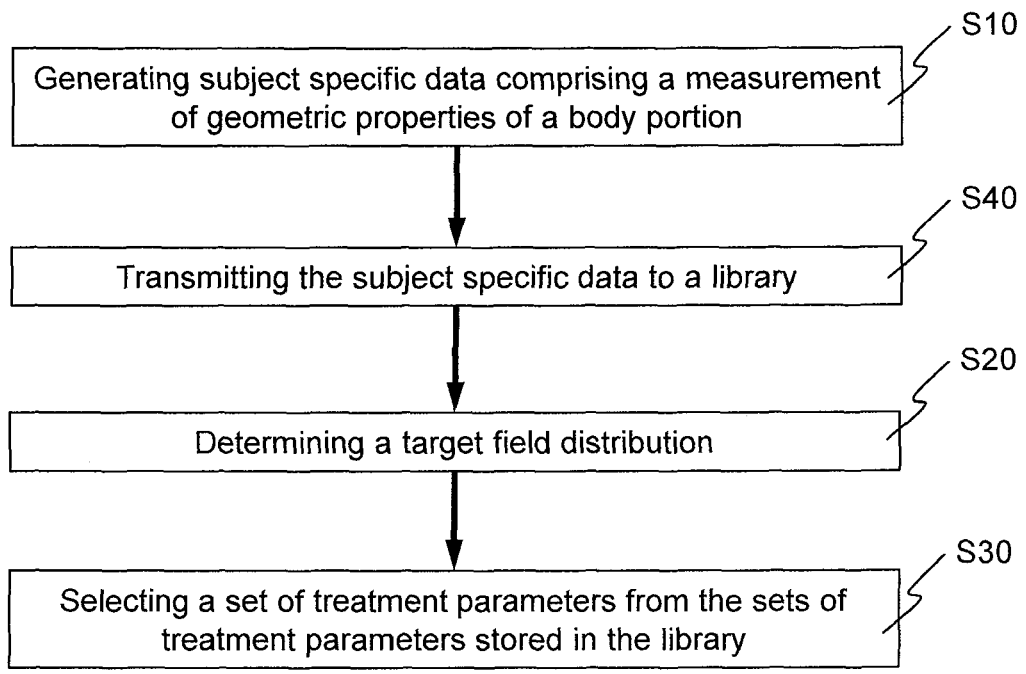
Figure 3:
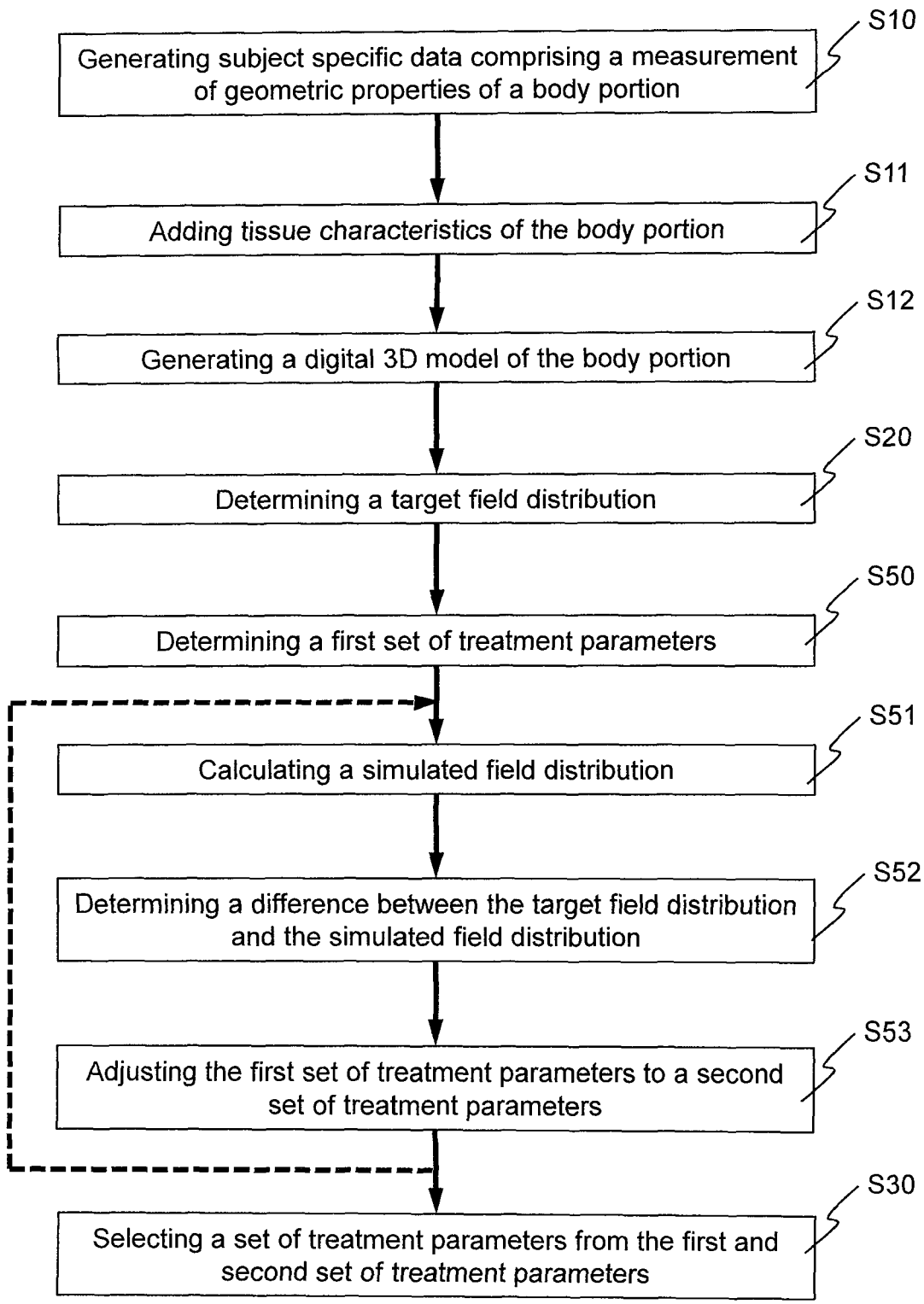
Figure 4:
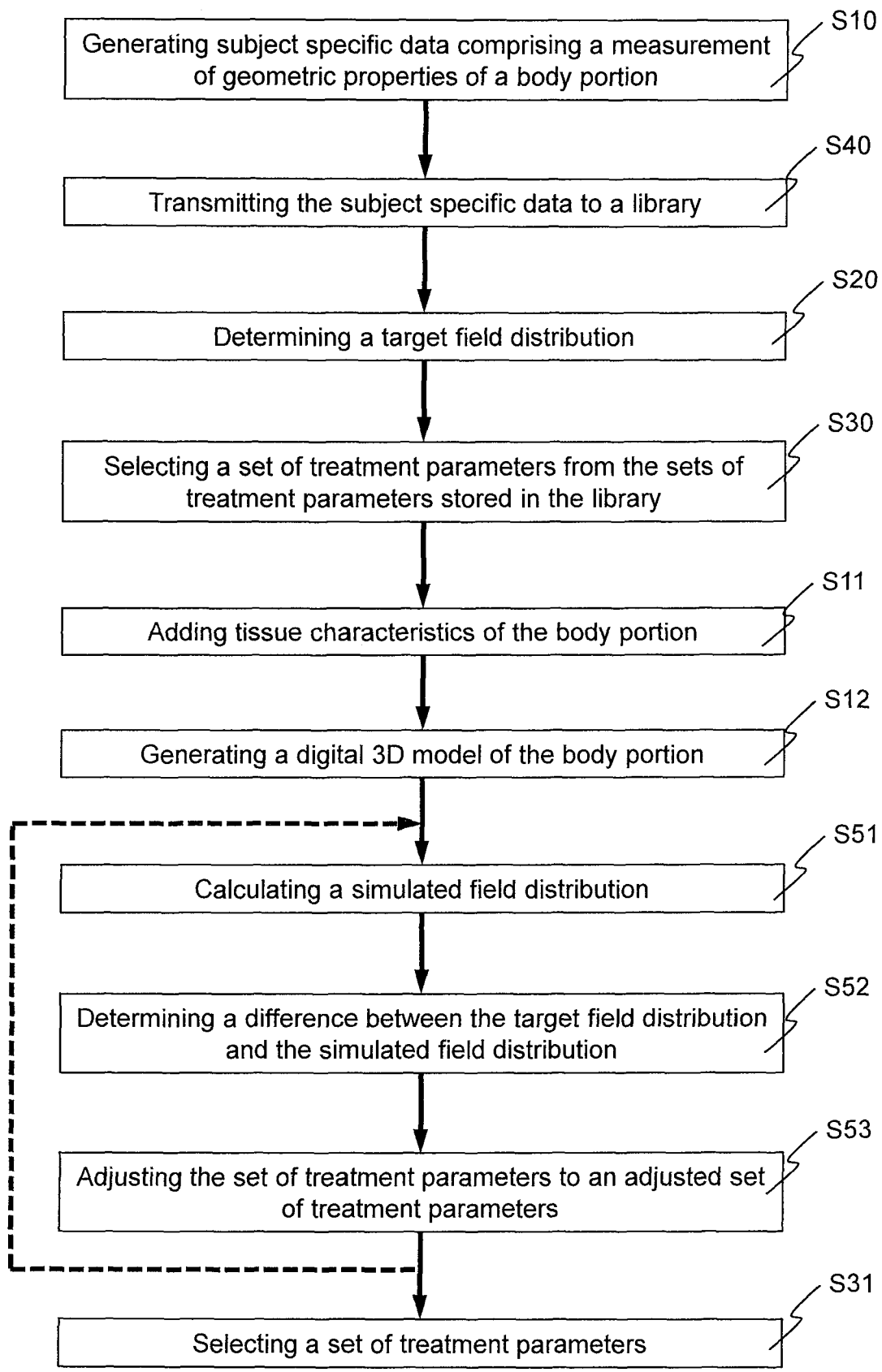
Figure 5:
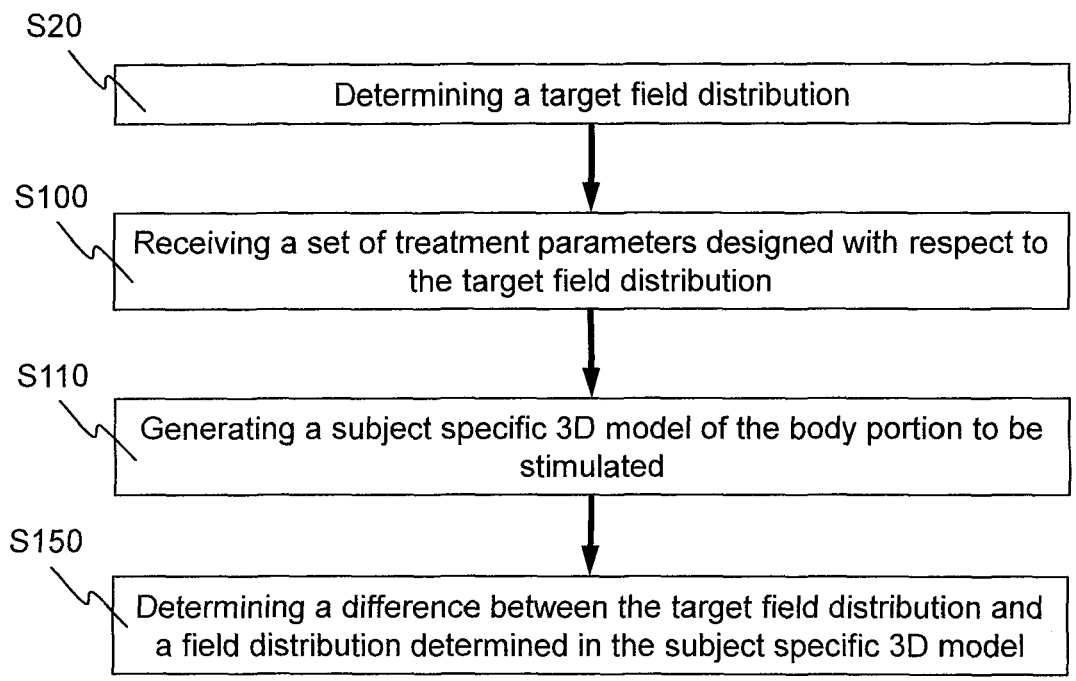
Figure 7:
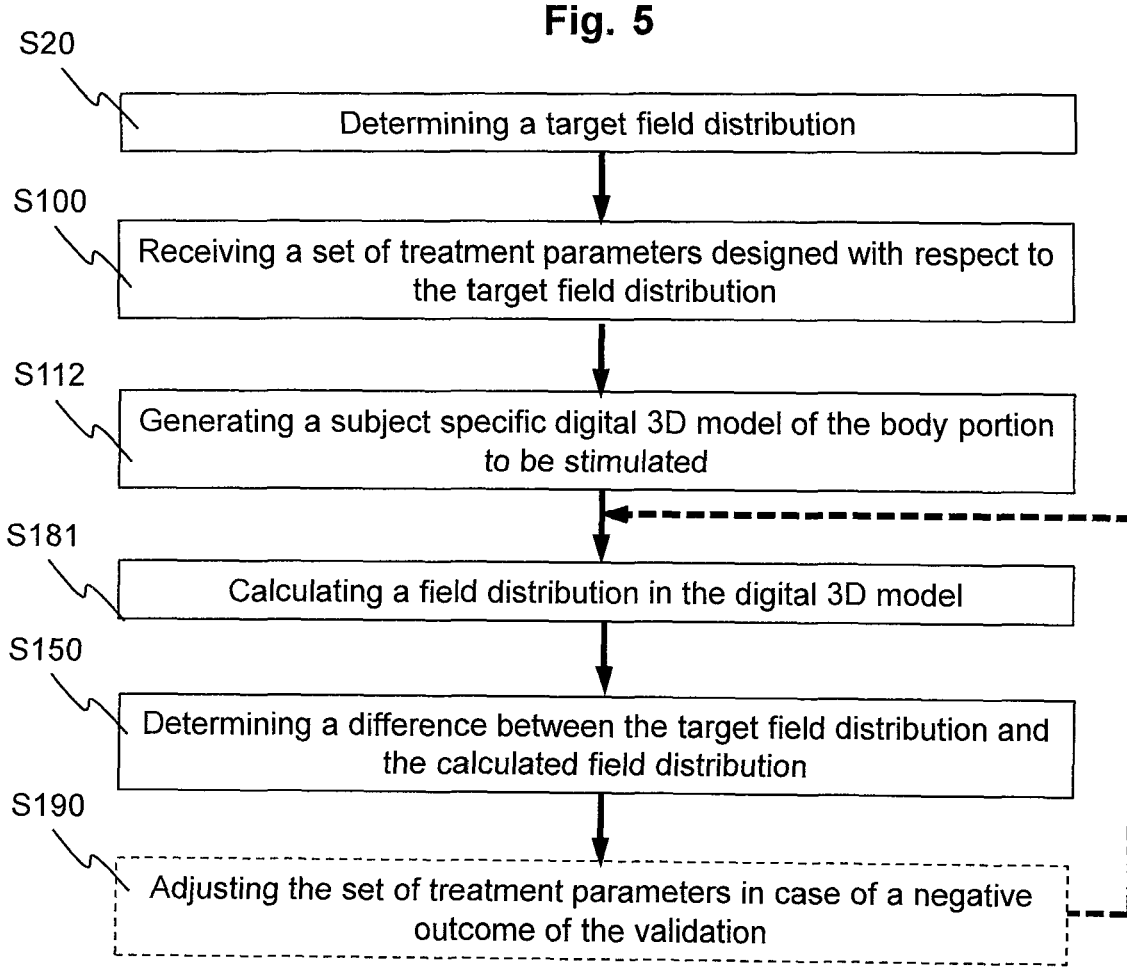
Figure 6:
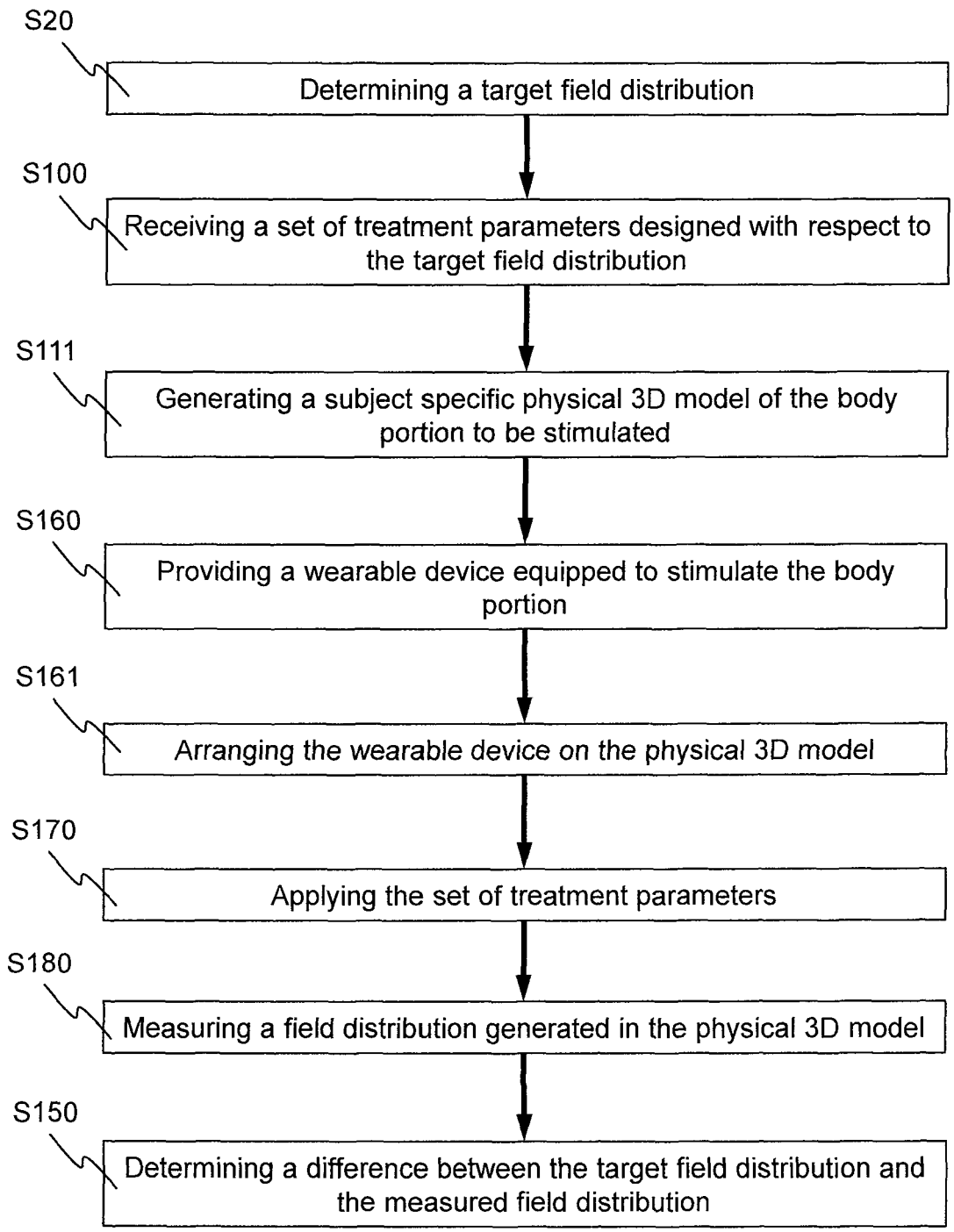

The subject matter of the invention will be explained in more detail in the following text with reference to exemplary embodiments that are illustrated in the attached drawings, which schematically show:

FIG. 1 a flow chart of steps that are common to a plurality of embodiments of a method for determining a subject specific set of treatment parameters for acoustic wave stimulation according to the first aspect of the invention;

FIG. 2 a flow chart of an embodiment of the method for determining a subject specific set of treatment parameters for acoustic wave stimulation;

FIG. 3 a flow chart of another embodiment of the method for determining a subject specific set of treatment parameters for acoustic wave stimulation;

FIG. 4 a flow chart of yet another embodiment of the method for determining a subject specific set of treatment parameters for acoustic wave stimulation;

FIG. 5 a flow chart of steps that are common to a plurality of embodiments of a method for validating a set of treatment parameters for acoustic wave stimulation according to the second aspect of the invention;

FIG. 6 a flow chart of an embodiment of the method for validating a set of treatment parameters for acoustic wave stimulation;

FIG. 7 a flow chart of another embodiment of the method for validating a set of treatment parameters for acoustic wave stimulation;

FIG. 8 a flow chart of a manufacturing process for a subject specific carrier element; and FIGS. 9-10 two exemplary embodiments of a subject specific carrier element.

DETAILED DESCRIPTION OF THE INVENTION

FIG. 1 shows a flow chart of steps of a method for determining a subject specific set of treatment parameters for acoustic wave stimulation. This means, FIG. 1 shows the basic steps of a method according to the first aspect of the invention. The steps shown are common to a plurality of embodiments of the method for determining a subject specific set of treatment parameters.

Subject specific data is generated in a first step S10. This step S10 of generating subject specific data includes the measurement of at least one geometric property of a body portion of the subject, said body portion being the body portion to be stimulated.

The geometric property include the shape of the body portion, at least. The shape can be measured by a method as described above (in particular one of the methods including "taking two pictures", "providing a wearable device" that is accordingly equipped, using medical imaging methods such as MRI, CT or a body scanner) or by a combination of such methods, for example.

The geometric property can include further information concerning the inner structure of the body portion. Information concerning the inner structure can be generated by a method as describe above (in particular one of the methods including "applying acoustic waves" and using medical imaging methods such as MRI or CT) or by a combination of such methods, for example.

The subject specific data can include further information, such as gender, age, weight, height, BMI, body fat content, fat percentage, muscle percentage etc.

A target field distribution of the acoustic field in the body portion is determined in a step S20 subsequent to the step of generating subject specific data. In other words, a distribution of the acoustic field in the body portion is determined, wherein the distribution is capable to stimulate the body portion in a manner that a desired effect is generated. Hence, the step S20 of determining a target field distribution includes generally the substep of selecting an application.

Depending on the application and the body portion, the target field distribution can include a focused spot at a measured or expected position of neurons or at the measured or expected position of a portion of the body portion, such as a muscle or a tendon, for example.

The target field distribution can be determined based on at least one of the measurement of the geometric property of the body portion, in particular when including information concerning the inner structure of the body portion including information concerning the nervous system, experience of a practitioner, supplementary material relating applications with target field distributions, and consulting a library, wherein the library can be automated in the sense that it determines a target field distribution from input given by a user. The library can be an electronic library as described above and below.

A set of treatment parameters is selected from at least two sets of treatment parameters in a step S30 subsequent to the step of determining a target field distribution.

Generally, a set of treatment parameters includes (i) operating parameters for at least one transducer equipped for generating an acoustic field for stimulation and (i) the position of the at least one transducer relative to the body portion.

There are various sets of treatment parameters that are able to generate a field distribution in the body portion that approximates the target field distribution in a good manner.

Various selection criteria can be considered in the step S30 of selecting a set of treatment parameters from at least two sets of treatment parameters. For example, at least one of the following criterion can be considered:

Possibilities to arrange the at least one transducer on the body portion;

Knowledge about success of sets of parameters potentially suitable for the application selected;

Knowledge about side effects of sets of parameters potentially suitable for the application selected;

Differences between the body portion to be stimulated and the body portion on which the determination of the target field distribution is relied.

Said differences can be in the geometric property or properties of the body portion, in its tissue characteristics and/or in other subject specific data (e.g., gender, age, weight, height, BMI, body fat content, fat percentage, muscle percentage), for example.

FIG. 2 shows a flow chart of an exemplary embodiment of the method for determining a subject specific set of treatment parameters for acoustic wave stimulation.

In this embodiment, an electronic library ("library" in the following) is used in the step S20 of determining a target field distribution and in the step S30 of selecting a set of treatment parameters. Hence, the method shown includes a step 40 of transmitting subject specific data to the library.

In particular, the subject specific data generated in the step S10 of generating subject specific data and including information concerning the geometric property of the body portion are transmitted.

The application selected in the step S20 of determining a target field distribution can be transmitted to the library as well. Alternatively, the electronic library can be combined with a user interface as described above. The user interface can be configured to help the user selecting the desired application.

In the embodiment shown, the library is in communication to a computer.

The computer can be configured to select the target field distribution of the target field distributions stored in the library that is expected to give the best results for the application selected.

The computer can be configured to apply the selection criteria on which the step S30 of selecting a set of treatment parameters bases. In particular, the computer can be configured to select the set of treatment parameters of the sets of treatment parameters stored in the library that is expected to generate a field distribution that approximates the target field distribution better than the expected field distributions generated by the other sets of treatment parameters.

FIG. 3 shows a flow chart of another exemplary embodiment of the method for determining a subject specific set of treatment parameters for acoustic wave stimulation.

Calculations, in particular numerical simulations, are used in the exemplary embodiment shown to determine a subject specific set of treatment parameters that generates a field distribution that is expected to approximate the target field distribution in a manner sufficient for the application selected.

Therefore, the method shown includes a step S11 of adding tissue characteristics of the body portion to the measured geometric property of the body portion.

The tissue characteristics can be measured by a method as describe above (in particular one of the methods including "applying acoustic waves" and "applying light tomography") or by a combination of such methods. Alternatively or in addition, approximate tissue characteristics that result from functions describing a specific material or from stored characteristics representing a tissue can be used, for example.

The method shown includes the further step S12 of generating a digital (i.e., virtual) 3D model of the body portion.

In the embodiment shown, the digital 3D model is a model of the measured geometrical properties to which the tissue characteristics are added, wherein the model is represented in a manner usable for numerical simulations. For example, it can be represented as needed by commercially available numerical simulation programs, such as Comsol Multiphysics by Comsol or Ansys by CADFEM, for example.

Optionally, the digital 3D model or information related to it can be used to determine the target field distribution. The target field distribution can be determined by use of the library.

In this case, the computer that is in communication with the library can be configured to determine a target field distribution in the digital 3D model, for example by adapting field distributions stored for similar digital 3D models. This can result in a target field distribution that is of high quality with respect to the application and the body portion.

The method shown in FIG. 3 includes the further step S50 of determining a first set of treatment parameters. For example, the first set of treatment parameters can be derived from the target field distribution by a practitioner or by the subject, optionally supported by supplementary material including information relating field distributions to sets of parameters, or in an automated manner, for example by a computer configured to determine a set of treatment parameters from stored sets of treatment parameters. The computer can be the computer in communication with the library and the sets of treatment parameters can be stored in the library.

Depending on the number of treatment parameters and target field distributions stored, one can also envisage that the computer is configured to calculate the first set of treatment parameters.

The digital 3D model and the first set of treatment parameters is used as input for a step S51 of calculating a calculated field distribution, in the embodiment shown.

In the embodiment shown, the calculation includes carrying out a numerical simulation.

The method shown includes the further step S52 of determining a difference between the target field distribution and the calculated field distribution and the further step S53 of adjusting the first set of treatment parameters to a second set of treatment parameters.

The step S51 of calculating a calculated field distribution, the step S52 of determining a difference and the step S53 of adjusting can be repeated in order to determine various sets of treatment parameters that generate field distributions that approximate the target field distribution. Said repetitions are indicated in FIG. 3 by a dashed arrow.

Ideally, the repetitions are iterations improving the degree of approximation of the target field distribution continuously.

The step S53 of adjusting can store the differences determined in order to determine if an adjustment leads to an improvement or not. The differences stored can be used further in the step S30 of selecting a set of treatment parameters.

Finally, the method shown in FIG. 3 includes the step S30 of selecting a set of treatment parameters, which is selecting the set of treatment parameters leading to a calculated field distribution that has the smallest difference to the target field distribution, in the embodiment shown. In the simple case with one repetition only, this means selecting a set of treatment parameters form the first and second set of treatment parameters.

The embodiment of FIG. 3 can be considered as an exemplary embodiment of the method for validating a set of treatment parameters for acoustic wave stimulation (second aspect), too. This is because it includes the step S12 of generating a 3D model of the body portion to be stimulated (namely a digital 3D model) that can be subject specific, and the step S52 of determining a difference between the target field distribution and a field distribution determined (namely simulated) in the 3D model (the digital 3D model) that can be subject specific, wherein said steps allow for checking the congruence between the field distribution that is expected to be generated by a set of treatment parameters and the target field distribution.

FIG. 4 shows a flow chart of yet another exemplary embodiment of the method for determining a subject specific set of treatment parameters for acoustic wave stimulation.

In this embodiment, the step S30 of selecting is not necessarily the final step of the method. However, the method can include optionally a further step S31 of selecting that can be the final step of the method.

The method shown includes the optional final step S31 of selecting and the preceding steps providing sets of treatment parameters from which can be selected in particular in cases in which the set of treatment parameters selected in the first step S30 of selecting is expected to result in a set of treatment parameters that leads to a field distribution that approximate the target field distribution in an insufficient manner only. For example, this can be the case if at least one of the following applies:

The subject specific data transmitted to the library are not sufficient to determine a target field distribution and/or a set of treatment parameters that is specific enough for the subject.

The set of parameters and/or the field distributions stored approximate the subject specific application in a rough manner only.

The method used for determining the target field distribution is not sophisticated enough.

More in detail, the method shown in FIG. 4 includes the step S10 of generating subject specific data including the measurement of at least one geometric property of the body portion to be stimulated, the step S40 of transmitting subject specific data to the library, the step S20 of determining the target field distribution and the step S30 of selecting a set of treatment parameters.

These steps are carried out in any embodiment described with respect to FIGS. 1-3, wherein the set of treatment parameters is selected from the sets of treatment parameters stored in the library.

The method shown includes the step S11 of adding tissue characteristics of the body portion to the measured geometric property of the body portion and the step S12 of generating the digital 3D model of the body portion. These steps can be carried out according to any embodiment described with respect to FIG. 3.

In the embodiment shown, the step S11 of adding and the step S12 of generating the digital 3D model are not used for determining the target field distribution or for selecting the set of treatment parameters from the sets of treatment parameters.

Rather, the step S11 of adding and the step S12 of generating the digital 3D model are used to determine if the selected set of treatment parameters fits in a sufficient manner to the subject specific case. This is done in the method shown by including the step S51 of calculating a calculated field distribution from the selected set of treatment parameters and for the subject specific digital 3D model of the body portion and by including the step S52 of determining a difference between the target field distribution and the calculated field distribution.

Optionally the target field distribution can be adapted to differences observed between the geometric property and/or tissue characteristics of the body portion to be stimulated and the geometric property and/or tissue characteristics on which the determined target field distribution bases (not shown).

If the method includes the optional step of adapting the target field distribution, the step S52 of determining a difference can determine a difference between the adjusted target field distribution and the calculated field distribution.

If the difference determined in the step S52 of determining a difference is larger than a preset value, the method shown includes the step S53 of adjusting the set of treatment parameters to an adjusted set of treatments parameters, independent on the concrete realization of the step S52 of determining the difference.

The step S51 of calculating, the step S52 of determining a difference and the step S53 of adjusting can be in any embodiment described with respect to FIG. 3, wherein the step S53 of adjusting can include the substep of storing the difference and/or the substep of transmitting the difference determined to the library.

The step S51 of calculating, the step S52 of determining a difference and the step S53 of adjusting can be repeated as described with respect to FIG. 3. The repetitions leading in various sets of treatment parameters that generate field distributions that approximate the target field distribution are indicated in FIG. 3 by a dashed arrow.

If the method shown includes the step S53 of adjusting the set of treatment parameters to an adjusted set of treatment parameters, the method can include the further step S31 of selecting a set of treatment parameters, wherein the set of treatment parameters is selected from the adjusted set(s) of treatment parameter and the set of treatment parameters selected from the sets of treatment parameters stored in the library.

The embodiment of FIG. 4 can be considered as an exemplary embodiment of the method for validating a set of treatment parameters for acoustic wave stimulation (second aspect), too. This is because it includes the step S12 of generating a 3D model of the body portion to be stimulated (namely a digital 3D model) that can be subject specific, and the step S52 of determining a difference between the target field distribution and a field distribution determined (namely simulated) in the 3D model (the digital 3D model) that can be subject specific, wherein the steps allow for checking the congruence between the field distribution that is expected to be generated by a set of treatment parameters and the target field distribution.

FIG. 5 shows a flow chart of steps of a method for validating a set of treatment parameters for acoustic wave stimulation. This means, FIG. 5 shows steps of a method according to the second aspect of the invention. The steps shown are common to a plurality of embodiments of the method for validating a set of treatment parameters.

The method includes a step S20 of determining a target field distribution. This step can be carried out in any embodiment described with respect to FIGS. 1-4.

The method includes further a step S100 of receiving a set of treatment parameters. It is this set of treatment parameters received that is validated by the method. This also means that the received set of treatment parameters is designed with respect to the target field distribution. In other words, the received set of treatment parameters is designed to generate a field distribution that approximates the target field distribution. The degree of approximation depends on various aspects, such as the differences in the geometric property and/or tissue characteristics between the body portion based on which the target field distribution has been determined and the body portion to be stimulated, the procedure chosen to determine or design the set of treatment parameters etc.

The set of treatment parameter received can be a set of treatment parameters that has been determined in any embodiment described with respect to FIGS. 1-4, for example.

The method includes further a step S110 of generating a subject specific 3D model of the body portion to be stimulated. This step can be carried out in any embodiment described with respect to FIGS. 1-4 and that is subject specific, this means that it includes at least one information of the subject that is relevant for the overall characteristics of the subject specific 3D model. In particular, the at least one relevant information is the geometric property, this means at least the shape, of the body portion. The subject specific 3D model can include tissue characteristics of the body portion to be stimulated.

The method for validation bases on determining a difference between the target field distribution and a field distribution determined in the subject specific 3D model of the body portion to be stimulated.

The 3D model can be a physical ("real") 3D model as it is the case in the embodiment of FIG. 6 or a digital ("virtual") 3D model as it is the case in the embodiment of FIG. 7.

The method includes a step S150 for determining a difference between the target field distribution and the field distribution determined in the subject specific 3D model of the body portion to be stimulated.

The difference determined can be used to decide whether the received set of treatment parameters leads to a field distribution in the body portion that fits the target field distribution in a manner that is sufficient for being applied to the body portion and for the selected application or not.

FIG. 6 shows a flow chart of an exemplary embodiment of the method for validating a set of treatment parameters for acoustic wave stimulation. In the embodiment shown, a subject specific physical 3D model of the body portion to be stimulated and a field distribution measured in the subject specific physical 3D model, said measured field distribution being generated by the received set of treatment parameters, is used in the method for validating.

The method shown includes a step S111 of generating a subject specific physical 3D model of the body portion to be simulated. In other words, it is a subject specific physical 3D model that is generated in the step S110 of generating a subject specific 3D model of the method shown in FIG. 5.

The method of FIG. 6 includes further a step S160 of providing a wearable device equipped to stimulate the body portion and hence equipped to stimulate the subject specific physical 3D model of the body portion.

In particular, the wearable device includes the at least one transducer equipped for generating an acoustic wave in the body portion. This means, the wearable device includes the at least one transducer that is equipped to generate an acoustic field distribution in the body portion.

The wearable device is donned on the subject specific physical 3D model in a step S161 of arranging the wearable device on the subject specific physical 3D model.

The wearable device is arranged on the subject specific physical 3D model in a manner that the at least one transducer is arranged relative to the subject specific physical 3D model according to the received set of treatment parameters. Alternatively, the at least one transducer can be rearranged on the wearable device in a manner that it is arranged relative to the subject specific physical 3D model according to the received set of treatment parameters after rearrangement of the at least one transducer.

The relative arrangement of the at least one transducer can be considered as a first substep of a step S170 of applying the received set of treatment parameters to the at least one transducer equipped to generate an acoustic field in the body portion.

The step S170 of applying the set of treatment parameters includes a second substep of applying operating parameters according to the received set of treatment parameters to the at least one transducer. This substep is carried out after the first substep of arranging the at least one transducer relative to the body portion.

Further, the method shown includes a step S180 of measuring a field distribution generated in the subject specific physical 3D model. This can be done by reading out a grid of sensors integrated in the physical 3D model or by moving a sensor to different positions in the physical 3D model and reading out a field characteristic, such as its intensity, at each position, for example.

A difference between the measured field distribution and the target field distribution is determined in the step S150 of determining a difference between the target field distribution and a field distribution determined in the subject specific 3D model (which is the subject specific physical 3D model in the embodiment shown).

FIG. 7 shows a flow chart of a further exemplary embodiment of the method for validating a set of treatment parameters for acoustic wave stimulation. In the embodiment shown, a subject specific digital 3D model of the body portion to be stimulated and a field distribution calculated in the subject specific digital 3D model is used in the method for validating, wherein the field distribution generated in the subject specific digital 3D model by the received set of treatment parameters is calculated.

The method shown includes a step S112 of generating a subject specific digital 3D model of the body portion to be simulated. In other words, it is a subject specific digital 3D model that is generated in the step S110 of generating a subject specific 3D model of the method shown in FIG. 5.

The step S112 of generating a subject specific digital 3D model can be carried out according to any embodiment disclosed with respect to FIGS. 1-4.

The method of FIG. 7 includes further a step S181 of calculating the field distribution generated by the received set of treatment parameters in the digital 3D.

The step S181 of calculating the field distribution includes carrying out a numerical simulation. The numerical simulation can be set up and run in any embodiment described above in relation to a numerical simulation used for calculating a field distribution in the body portion.

A difference between the calculated field distribution and the target field distribution is determined in the step S150 of determining a difference between the target field distribution and a field distribution determined in the subject specific 3D model (which is the subject specific digital 3D model in the embodiment shown).

FIG. 7 shows as an optional feature a step S190 of adjusting the received set of treatment parameters. Such a step of adjusting can be part of any embodiment of the method of validating, in particular the embodiments shown in FIGS. 5-7, in case the validation of the received set of treatment parameters is negative, this means in case the set of treatment parameters received is considered not sufficient for being applied to body portion.

The step S190 of adjusting the received set of treatment parameters or of an adjusted set of treatment parameters, the step S181 of calculating a field distribution in the digital 3D model and the step S150 of determining a difference between the target field distribution and the calculated field distribution is repeated in order to determine a set of treatment parameters that passes the validation.

FIG. 8 shows a flow chart of an exemplary manufacturing process for a subject specific carrier element 1, this means a carrier element 1 including a rigid portion including a surface 17 that forms a negative of a surface of the body portion to be stimulated.

The essential step of the manufacturing process shown in FIG. 8 is the step S112 of generating a subject specific digital 3D model of the body portion to be stimulated, wherein said step 112 generates a model of the surface of the body portion to be stimulated or a portion of the surface of the body portion to be stimulated when used in the manufacturing process.

The step S200 of the actual production of the carrier element can include a rapid manufacturing process, such as milling, turning, casting or a rapid additive manufacturing process such as printing, for example 3D-printing.

In principle, the other steps shown in FIG. 8 are optional. However, they are needed if the carrier element 1 manufactured includes a limited number of positions at which the at least one transducer can be mounted or if the carrier element 1 manufactured includes a fixation element 10 at the target position for each transducer needed in a specific application.

A target position of a transducer is a position of the transducer relative to the body portion, said position being required to generate the target field distribution in the body portion when the set of treatment parameter is applied. In many embodiments, the target position(s) is/are part of the set of treatment parameters.

FIG. 9 shows two different views of an exemplary embodiment of a subject specific carrier element 1 that is manufactured by the process shown in FIG. 8, for example.

The carrier element 1 includes a portion 16 of rigid material that forms the negative of the body portion to be stimulated, this means that it includes a surface 17 that forms the negative of the surface of the body portion to be stimulated.

A carrier element 1 is shown in a simplified manner that fits to the forearm of a specific user.

The carrier element 1 of FIG. 9 is not only specific to a subject, this means it does not only include a surface 17 that forms a nearly perfect negative of the forearm of that subject (but generally not of another subject), but it is also specific to a treatment. This means, the fixation element 10 and the transducer (when mounted to the carrier element 1) have a position that corresponds to a target position of a specific treatment after mounting the carrier element 1 on the body portion.

It goes without saying that one can envisage a carrier element 1 as shown in FIG. 9 but including a plurality of fixation elements each of them at position that corresponds to a target position of specific treatment after mounting the carrier element 1 on the body portion.

FIG. 10 shows another exemplary embodiment of a subject specific carrier element 1 that is manufactured by the process shown in FIG. 8, for example.

The carrier element 1 shown differs from the carrier element 1 shown in FIG. 9 by including a plurality of fixation elements 10. This means that the carrier element 1 of FIG. 10 is specific to a user but not specific to a treatment. Rather, the transducers can be mounted at positions and in a number that correspond to the set of treatment parameters for one of various possible treatments.

Mounting of the transducers can be supported by markers arranged on the carrier element, for example.

Alternatively, the transducers can be firmly mounted to the fixation elements 10 and a controller of the treatment device can be configured to activate the transducers as indicated by the set of treatment parameters.

The invention claimed is:

1. A computer-implemented method for determining a subject specific set of treatment parameters for acoustic wave stimulation comprising the steps of:
generating subject specific data, wherein the step of generating subject specific data comprises measuring a geometric property of a body portion;
determining a target field distribution in the body portion, wherein the step of determining a target field distribution comprises selection of an application;
further comprising a step of selecting a set of treatment parameters from at least two different sets of treatment parameters, wherein the step of selecting a set of treatment parameters is made prior to a step of applying any set of treatment parameters to the body portion;
wherein the step of selecting a set of treatment parameters comprises a comparison of a first expected field distribution related to a first set of treatment parameters with the target field distribution and a comparison of a second expected field distribution related to a second set of treatment parameters with the target field distribution.

2. The method of claim 1, wherein at least one of the geometric property measured and subject specific information is considered in the step of selecting a set of treatment parameters.

3. The method of claim 1, comprising the further step of measuring neuronal activity of the body portion and/or measuring electrical activity of the body portion.

4. The method of claim 1, comprising further the step of providing a wearable device comprising at least one transducer, the step of arranging the wearable device at the body portion, and a step of reading out a position of the at least one transducer relative to the body portion.

5. A computer-implemented method for determining a subject specific set of treatment parameters for acoustic wave stimulation comprising the steps of:
generating subject specific data, wherein the step of generating subject specific data comprises measuring a geometric property of a body portion;
determining a target field distribution in the body portion, wherein the step of determining a target field distribution comprises selection of an application;
further comprising a step of selecting a set of treatment parameters from at least two different sets of treatment parameters, wherein the step of selecting a set of treatment parameters is made prior to a step of applying any set of treatment parameters to the body portion;
wherein the step of generating subject specific data comprises the steps of:
adding tissue characteristics of the body portion to the measured geometric property;
generating a digital 3D model of the body portion based on the measured geometric property and on the added tissue characteristics.

6. The method of claim 5, further comprising the steps of:
determining a first set of treatment parameters;
calculating a calculated field distribution of the acoustic field in the body portion using the digital 3D model of the body portion and the first set of treatment parameters;
determining a difference between the calculated field distribution and the target field distribution;
adjusting the first set of treatment parameters to a second set of treatment parameters;
wherein the step of selecting a set of treatment parameters comprises selecting from the first and second set of treatment parameters.

7. The method of claim 6, wherein the step of calculating a calculated field distribution, the step of determining a difference between the calculated field distribution and the target field distribution and the step of adjusting the first set of treatment parameters are repeated until the difference between the calculated field distribution and the target field distribution is smaller than a preset value.

8. A computer-implemented method for determining a subject specific set of treatment parameters for acoustic wave stimulation comprising the steps of:
generating subject specific data, wherein the step of generating subject specific data comprises measuring a geometric property of a body portion;
determining a target field distribution in the body portion, wherein the step of determining a target field distribution comprises selection of an application;
further comprising a step of selecting a set of treatment parameters from at least two different sets of treatment parameters, wherein the step of selecting a set of treatment parameters is made prior to a step of applying any set of treatment parameters to the body portion; and
comprising the further step of transmitting the subject specific data to an electronic library, wherein the electronic library is configured to carry out the step of determining a target field distribution and the step of selecting a set of treatment parameters.

9. A method for validating a set of treatment parameters for acoustic wave stimulation comprising the steps of:
determining a target field distribution of an acoustic field in a body portion to be stimulated;
receiving a set of treatment parameters for at least one transducer, wherein the set of treatment parameters is designed with respect to the target field distribution;
generating a subject specific 3D model of the body portion to be stimulated;
determining a difference between the target field distribution and a field distribution determined in the subject specific 3D model.

10. The method of claim 9, wherein the set of treatment parameters is received from an electronic library or wherein the set of treatment parameters are calculated.

11. The method of claim 9, wherein the subject specific 3D model is a subject specific physical 3D model.

12. The method of claim 11, comprising the steps of:
providing a wearable device comprising the at least one transducer;
arranging the wearable device on the physical 3D model;
applying the set of treatment parameters to the wearable device;
wherein the field distribution in the subject specific physical 3D model is determined by a measurement.

13. The method of claim 9, wherein the subject specific 3D model is a digital 3D model and wherein the field distribution in the subject specific digital model is determined by a numerical simulation.

14. The method of claim 9, comprising a step of adjusting the received set of treatment parameters if the difference between the target field distribution and the field distribution determined in the subject specific 3D model is larger than a preset value.

* * * * *